United States Patent [19]

Goldwasser et al.

[11] Patent Number: 4,711,240
[45] Date of Patent: Dec. 8, 1987

[54] SURGICAL DISSECTOR

[75] Inventors: Benad Goldwasser, Rochester, Minn.; Culley Carson, Durham, N.C.

[73] Assignee: Duke University Patents Foundation, Durham, N.C.

[21] Appl. No.: 863,446

[22] Filed: May 15, 1986

[51] Int. Cl.4 ............................................. A61B 17/00
[52] U.S. Cl. .................................... 128/319; 128/325; 128/346; 81/419; 81/352; 81/362
[58] Field of Search ............... 128/319, 346, 321, 322, 128/303 R, 325; 81/424.5, 419, 352, 362

[56] References Cited

U.S. PATENT DOCUMENTS

| | | | |
|---|---|---|---|
| 1,756,670 | 4/1930 | Treat | 128/346 |
| 1,982,207 | 11/1934 | Furniss | 128/346 |
| 2,668,538 | 1/1952 | Baker . | |
| 3,315,679 | 1/1964 | Sarracino . | |
| 3,323,208 | 6/1967 | Hurley . | |
| 3,367,336 | 2/1968 | Eizenberg | 128/321 |
| 3,503,397 | 3/1970 | Fogarty et al. | 128/346 X |
| 3,515,139 | 6/1970 | Mallina | 128/346 X |
| 3,683,925 | 8/1972 | Frankel . | |
| 3,951,138 | 4/1976 | Akopov . | |
| 4,112,951 | 9/1978 | Hulka et al. . | |
| 4,120,303 | 10/1978 | Villa-Massone et al. | 128/330 |
| 4,205,681 | 6/1980 | Nestor et al. . | |
| 4,424,811 | 1/1984 | Groot . | |
| 4,558,699 | 12/1985 | Bashour | 128/346 |
| 4,605,002 | 8/1986 | Rebuffat | 128/346 X |

FOREIGN PATENT DOCUMENTS

| | | |
|---|---|---|
| 18698 | 11/1980 | European Pat. Off. . |
| 1202436 | 10/1965 | Fed. Rep. of Germany . |
| 2308496 | 8/1974 | Fed. Rep. of Germany . |
| 316794 | 4/1934 | Italy . |
| 187262 | 2/1937 | Switzerland . |

*Primary Examiner*—Michael H. Thaler
*Attorney, Agent, or Firm*—Oblon, Fisher, Spivak, McClelland & Maier

[57] ABSTRACT

A surgical dissector has parallel arms mounted by a scissors linkage for moving toward and away from one another while remaining parallel. A plurality of teeth extend transversely from the arms and are positioned so that they may be interdigitated when the dissector is in a closed position. The teeth have rounded distal ends and are sufficient spaced so that spaces remain between the interdigitated teeth. The dissector is particularly useful in partial kidney resectioning.

9 Claims, 6 Drawing Figures

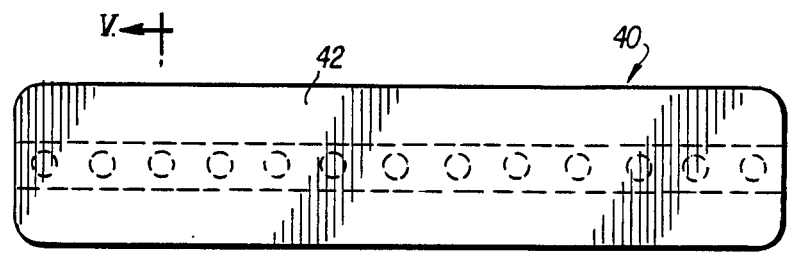
FIG. 3
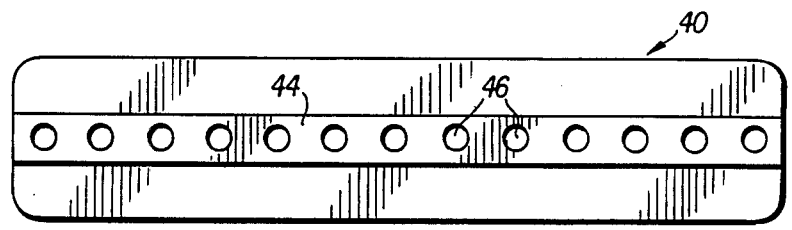
FIG. 4
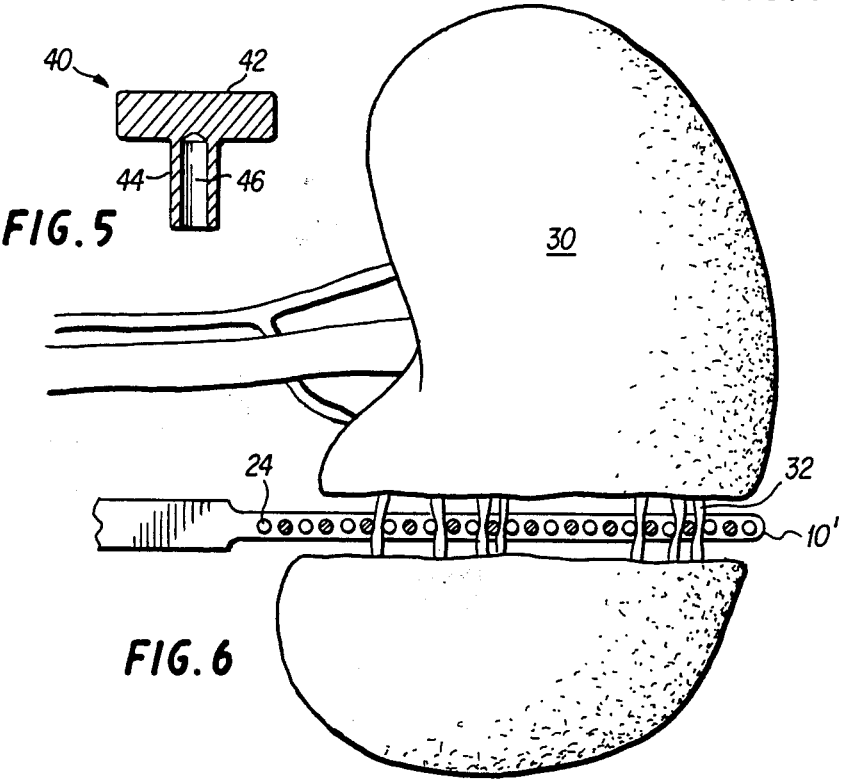
FIG. 5
FIG. 6

SURGICAL DISSECTOR

BACKGROUND OF THE INVENTION

1. Field of the Invention

The present invention relates to a surgical dissector. More particularly, the present invention relates to a dissector useable in the performance of surgical procedures on spongy organs made of pulpy, friable tissue, through which course blood vessels and ducts of various sizes. The invention is particularly adapted to the partial resectioning of a kidney, however it is also useful in the performance of nephrotomies, hepatectomies and pancreatectomies.

2. Brief Discussion of the Related Art

Surgical operations on spongy organs made of pulpy, friable tissues through which course blood vessels and ducts introduce unique problems, particularly where it is necessary to resection the organs without excessive bleeding from the blood vessels or other discharge from the ducts. It is therefore desirable to be able to identify and individually ligate the blood vessels and other ducts after incisions into the organ. Conventionally, this has been found to be difficult, and as a result such blood vessels and other ducts were cut with accompanying bleeding and fluid loss. Mass suture ligation of tissue was then necessary for hemostasis.

An effort to solve this problem has been described in Tien-Yu Lin, "A Simplified Technique for Hepatic Resection. The Crush Method", *Annals of Surgery* 180: 285–290, 1974. Lin describes a hepatic libectomy which uses a liver crush clamp to fracture the friable liver tissue using a "crush method." A liver crush clamp in the form of a scissors having short teeth on one of its jaws was tightly applied to the liver near the intended position of an incision line. After incision, the clamp was introduced into the rent liver and repeatedly tightly applied in order to crush liver tissue after which the crushed liver tissue was removed, leaving the hepatic artery, portal vein branches and hepatic duct exposed. Following ligation of the exposed tissue, the affected lobe was detached and the clamp loosened. In a partial resection of a liver, the unyielding vascular and ductile components appear as cord-like bridges connecting two parts of the liver, following a crushing operation, and they are individually ligated and divided.

However, the Lin clamp has certain deficiencies, particularly if used for surgical operations on a relatively thick organ such as a kidney. For example, in resectioning any spongy organ, the Lin clamp will apply pressure unevenly along the length of the scissors jaws. The scissors jaws will close more fully, and so apply greater pressure, near their joint than at their mid-point. As a result, blood vessels or other ducts closest to the scissors joint can be crushed and damaged while friable organ tissue further from this joint may not be sufficiently crushed to expose the blood vessels therein. Moreover, the relatively sharp teeth on one of the scissors jaws of the Lin clamp can puncture or further damage blood vessels. This can result in the aforementioned undesirable blood loss.

This problem is accentuated in a kidney resectioning due to the fact that the kidney is a relatively short and thick organ. The scissors-like action of the Lin clamp produces an even greater angling between the scissors jaws in the resectioning of such thick organs, so that pressure and closure degree differentials along the length of the jaws are increased and the likely damage to blood vessels, both due to this pressure/closure differential and to damage from the sharp teeth of the clamp, is increased.

SUMMARY OF THE INVENTION

It is an object of the present invention to provide a surgical dissector useful in surgical operations on spongy organs made of pulpy, friable tissue.

It is a further object of the present invention to provide a surgical dissector useful in surgical operations on spongy organs made of pulpy, friable tissues, through which course blood vessels and ducts of various calibers, without damaging the blood vessels and ducts.

It is a further object of the present invention to provide a surgical dissector useful in the partial resectioning of spongy organs made of pulpy, friable tissue, through which course blood vessels and ducts, by crushing the organ tissue without damaging the blood vessels and ducts.

It is a further object of the present invention to provide a surgical instrument useful in partial kidney resectioning procedures, which crushes the friable kidney tissue without damaging blood vessels and urine ducts coursing therethrough.

It is yet a further object of the present invention to provide a surgical dissector useful in nephrotomy procedures.

In order to carry out the above, and other, objects the present invention provides a surgical dissector having first and second parallel arms which are connected to be moveable toward and away from one another, but not to be translatable along their lengths, while remaining parallel to one another. A plurality of mutually parallel cylndrical teeth are mounted to project from a planar surface of each of the arms, each tooth extending transverse to the length of the respective arm on which it is mounted. The teeth on each arm form an array extending along the length of that arm. The teeth are positioned on the arms such that they may be mutually interdigitated when the arms are moved towards one another to a closed position.

The teeth have rounded distal ends and are evenly mutually spaced such that spaces are provided between the interdigitated teeth when the arms are in the closed position. The parallel action of the arms assures even pressure on renal tissue along the length of the arms. Blood and other vessels are pushed aside by the rounded ends of the teeth and are squeezed into the spaces between the teeth during closure, and so are not damaged.

In the performance of a nephrotomy, for example in stone surgery, an incision is formed on only one side of the kidney. The dissector of the present invention can be adapted for use in a nephrotomy by the addition of a flat plate mounted on one toothed arm. The flat plate protects the surface of the kidney against which it is pressed while the arm with the exposed teeth incises the kidney tissue on the opposing surface. The plate preferably has holes for a snug fit over the teeth and a completely flat and smooth surface on the side which contacts the kidney.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a top view of the flat plate, showing the flat surface thereof;

FIG. 4 is a bottom view of the flat plate of FIG. 3;

FIG. 5 is a sectional view of the flat plate of FIG. 3, seen along plane V—V; and FIG. 6 is a schematic illustration of the dissector of the present invention applied in a kidney resectioning procedure.

DETAILED DESCRIPTION OF THE PREFERRED EMBODIMENTS

Figure 1:
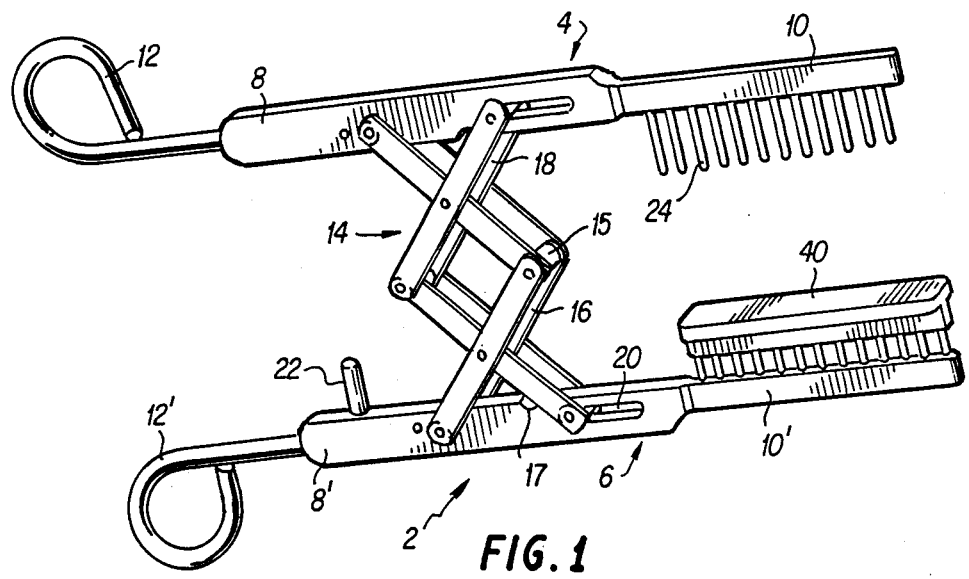
FIG. 1 is an orthogonal view of the dissector of the invention, illustrating the flat plate mounted thereon for use in a nephrotomy.

The surgical dissector of the present invention will now be described with reference to the figures wherein the same reference numerals are used to refer to the same or corresponding parts throughout the several views.

The surgical dissector 2 has first and second parallel arms 4 and 6, which are preferably formed of stainless steel. Each arm is preferably of square section and includes a connection portion 8 or 8' and a tooth support portion 10 or 10', as well as circular section handle portions 12 or 12'.

Connecting the arms 4 and 6 is a scissors linkage 14. The scissors linkage consists of parallel sets of first links 16 which are connected at one end, and whose other ends are pivoted to the connection portions of the respective arms 4 and 6 at fixed axes. Sets of second links 18 are linked at one end and have other ends slidable in slots 20 in the connection portions of the respective arms. The links 16 and 18 are pivoted to one another at their midpoints. The scissors linkage 14 constrains the arms to remain parallel to one another when moving toward or away from one another.

In the illustrated embodiment, two sets of linkages are provided, one on either side of the arms, and are connected at their midpoints by a connecting pivot pin and sleeve 15. Recesses 17 are provided in the arms to prevent pins connecting links 16 and 18 at their midpoints from interfering with the complete closure of the arms. If necessary for stability, connecting pivot pins and sleeves may also be provided at the link midpoints, in which case the recesses 17 may be enlarged to permit full closure of the arms. It is also possible to have a single set of first and second links or to have fewer or more links in each set, so long as the arms are constrained to remain parallel to one another during movement.

Figure 2:
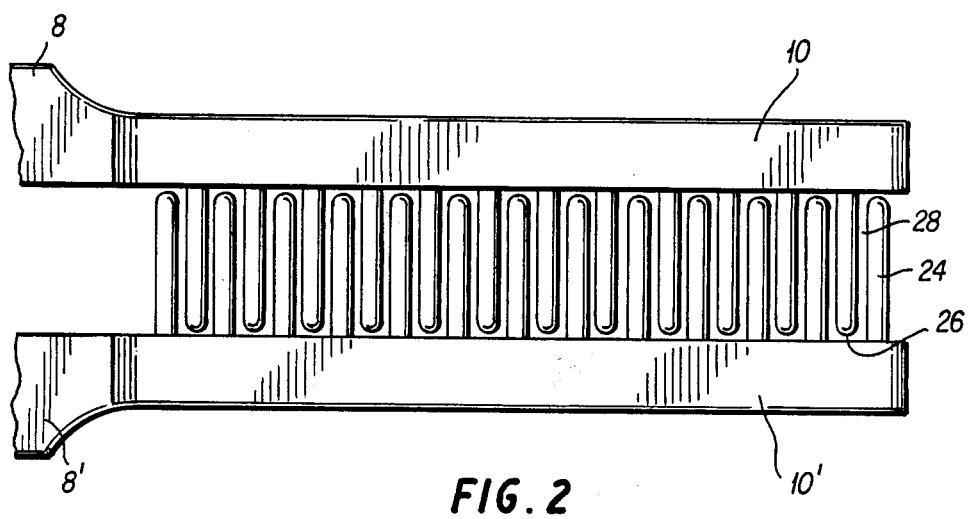
FIG. 2 is a detail of the parallel jaws in a closed position, illustrating the interdigitated teeth.

A cylindrical projection 22 on one of the arms fits in a corresponding bore (not shown) of the other arm to stabilize the dissector in its closed position, shown in FIG. 2, so that the teeth on the two arms are stably aligned as shown in FIG. 6.

As best seen in FIG. 2, each of the tooth support portions 10 or 10' is provided with a longitudinal array of teeth 24. Each of the teeth is cylindrical and extends from a substantially planar surface of its respective arm at 10 or 10' in a direction transverse to the length thereof. The distal end 26 of each of the teeth is rounded and can take the shape, for example, of a semicircle. The teeth 24 are evenly spaced on each of the arms and are mutually positioned such that they become interdigitated when the dissector is in the closed position shown in FIG. 2. Moreover, the teeth are sufficiently mutually spaced so that spaces 28 exist between the interdigitated teeth. The spacing of the teeth 24 should be such that the spaces 28 are essentially uniform along the length of the dissector.

The sizes of the teeth, arms and spaces are not critical, however the teeth should have a sufficient length and the spaces 28 a sufficient width such that blood vessels can be squeezed into the spaces 28 without damage during the closure of the dissector. Moreover, the scissors linkage 14 should permit sufficient separation for the arms so that the teeth 24 can be placed around an organ to be resectioned; for example, in the case of the resectioning of a kidney, when the arms are fully separated, the teeth should be separated by at least approximately 1.725 inches.

Although these dimensions are not critical, each of the teeth may be 0.590 inches in length and be mounted on each arm on 0.228 inch centers. Moreover, each cylindrical tooth may have a diameter of 0.093 inches, leaving a space of 0.135 inches between adjacent teeth on the same arm. As a result, the spaces 28 would each have a width of 0.021 inches and a length of 0.590 inches.

The use of the dissector as described above will now be described with reference to a partial kidney resection, although it is to be understood that the dissector is also adaptable to surgical procedures on other spongy organs.

The dissector is first positioned with the tooth support portions of the arms 4 and 6 on either side of the kidney 30 adjacent the resection plane. The arms are then closed so that the teeth 24 become interdigitated as shown in FIG. 2. During such closure, the tissue of the kidney 30 is crushed with even pressure, thereby exposing the blood vessels and urine ducts 32. The even pressure and rounded ends 26 of the teeth assures that the vessels and ducts 32 are not crushed. Rather, these rounded ends tend to push the vessels and ducts aside, so that they are squeezed into the spaces 28. This is best seen in FIG. 6 which shows only one of the two support portions 10'. The other tooth support portion is not illustrated, although it may be appreciated that alternate teeth 24 seen in FIG. 7 are in fact mounted to the nonillustrated tooth support portion 10.

The arms are repeatedly opened and closed four or five times, after which the renal tissue is completely crushed and the vessels and ducts 32 fully exposed as cords bridging the parts of the kidney. The vessels and ducts 32 can then be easily ligated, resulting in a partial kidney section with minimal blood loss.

In a nephrotomy to remove a kidney stone, an incision is made on only one side of the kidney. For this purpose, a flat plate 40 may be provided (FIGS. 4 through 6). The plate 40 is formed of stainless steel and has a smooth flat surface 42. Opposite the flat surface 42 is a ridge 44 having a plurality of bores 46. The bores 46 are shaped and sized so that the teeth 24 can snugly fit therein. The plate 40 is shown mounted on the teeth of the arm 6 in FIG. 1. The plate protects the surface of the kidney against which it is pressed while the arm 4 with the exposed teeth 24 incises the kidney tissue on the opposing surface.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A surgical dissector for crushing friable organ tissue, comprising:
   first and second parallel arms, each having an essentially planar surface;
   means for moving said first and second arms toward and away from one another while maintaining said arms parallel to one another; and
   a plurality of mutually parallel and cylindrical teeth mounted on and projecting from said planar surface of each of said first and second arms, said teeth on each of said arms projecting from said arm in a direction transverse to a length of said arm and forming an array extending along the length of said arm, all of said teeth having rounded distal ends and being positioned on said arms so as to be mutually interdigitated when said arms are moved toward one another to a closed position, wherein said teeth are positioned on said arms such that spaces are provided between said interdigitated teeth.

2. The dissector of claim 1 wherein said teeth are evenly spaced along said length of said arms.

3. The dissector of claim 1 including a plate having a flat surface and means for mounting said plate on one of said arms such that said flat surface faces said teeth of the other of said arms.

4. The dissector of claim 3 wherein said means for mounting comprise holes in a portion of said plate opposite said flat surface, said holes being postioned such that distal ends of said teeth may be fitted therein.

5. The dissector of claim 1 wherein said means for moving comprise a scissors linkage connecting said arms.

6. The dissector of claim 1 including handles on each of said arms.

7. The dissector of claim 1 including means for stabilizing said arms in said closed position such that said arrays of interdigitated teeth are substantially aligned.

8. The dissector of claim 7 wherein said means for stabilizing comprise a projection mounted on one of said arms and fittable in a hole in the other of said arms when said arms are in said closed position.

9. The dissector of claim 1 wherein said means for moving include means for constraining said arms against relative movement along their lengths.

* * * * *